(12) United States Patent
Tang et al.

(10) Patent No.: US 11,246,275 B2
(45) Date of Patent: Feb. 15, 2022

(54) METHOD FOR BREEDING SMALL-GRAIN STERILE RICE LINE AND SIMPLE METHOD FOR PRODUCING HYBRID RICE SEED

(71) Applicants: Hunan Agricultural University, Changsha (CN); HUNAN HOPING SEEDS SCIENCE & TECHNOLOGY INCORPORATED COMPANY, Changsha (CN)

(72) Inventors: Wenbang Tang, Changsha (CN); Yuedong Xiong, Changsha (CN); Xincai Ding, Changsha (CN); Guoliang Yi, Changsha (CN); Guihua Chen, Changsha (CN); Huabing Deng, Changsha (CN); Guilian Zhang, Changsha (CN); Yue Wang, Changsha (CN); Xingquan Ming, Changsha (CN); Qiang Xu, Changsha (CN); Ning Feng, Changsha (CN)

(73) Assignees: HUNAN AGRICULTURAL UNIVERSITY, Changsha (CN); HUNAN HOPING SEEDS SCIENCE & TECHNOLOGY INCORPORATED COMPANY, Changsha (CN)

( * ) Notice: Subject to any disclaimer, the term of this patent is extended or adjusted under 35 U.S.C. 154(b) by 160 days.

(21) Appl. No.: 16/638,758

(22) PCT Filed: Jul. 18, 2017

(86) PCT No.: PCT/CN2017/093249
§ 371 (c)(1),
(2) Date: Feb. 13, 2020

(87) PCT Pub. No.: WO2018/032925
PCT Pub. Date: Feb. 22, 2018

(65) Prior Publication Data
US 2020/0196545 A1    Jun. 25, 2020

(30) Foreign Application Priority Data
Aug. 17, 2016    (CN) .......................... 201610679340.0

(51) Int. Cl.
*A01H 1/02* (2006.01)
*A01H 6/46* (2018.01)
(Continued)

(52) U.S. Cl.
CPC ................. *A01H 1/02* (2013.01); *A01H 1/00* (2013.01); *A01H 5/10* (2013.01); *A01H 6/4636* (2018.05)

(58) Field of Classification Search
None
See application file for complete search history.

(56) References Cited

FOREIGN PATENT DOCUMENTS

| | | |
|---|---|---|
| CN | 101836580 A | 9/2010 |
| CN | 102124941 A | 7/2011 |

(Continued)

OTHER PUBLICATIONS

Wu et al. "Development of near-isogenic lines with different alleles of Piz locus and analysis of their breeding effect under Yangdao 6 background". Mol. Breeding. 36: 1-12. (Year: 2016).*

(Continued)

*Primary Examiner* — Matthew R Keogh
*Assistant Examiner* — David R Byrnes
(74) *Attorney, Agent, or Firm* — Bayramoglu Law Offices LLC

(57) ABSTRACT

A method for breeding a small-grain male-sterile rice line and a simple method for producing a hybrid rice seed are provided. The method for breeding the small-grain sterile (Continued)

rice line includes the following steps: crossing a female parent C815S with a male parent Qigui B to obtain a hybrid seed F1; planting the F1 and crossing the F1 with a female parent H155S to obtain a crossed hybrid seed F1'; planting the crossed hybrid seed F1' to obtain a F2' generation; planting an individual plant with ideal plant type, strong tillering, plant dwarf and small grain type from the F2' generation and a F3' generation, and then directional breeding more than two generations to obtain a seed with more than F5' generation as the small-grain sterile rice line.

7 Claims, 4 Drawing Sheets

(51) Int. Cl.
*A01H 1/00* (2006.01)
*A01H 5/10* (2018.01)

(56) References Cited

FOREIGN PATENT DOCUMENTS

| CN | 102948361 | A | * | 3/2013 |
|---|---|---|---|---|
| CN | 102948361 | A | | 3/2013 |
| CN | 105104167 | A | | 12/2015 |
| CN | 105532433 | A | * | 5/2016 |
| CN | 105532433 | A | | 5/2016 |
| CN | 106416997 | A | | 2/2017 |

OTHER PUBLICATIONS

Zhang, et al. "Analysis of Yield Traits in Conventional Rice Varieties". Agricultural Science and Technology. 17(4): 852-856. (Year: 2016).*

Yu-Peng, et al. "Phenotypic analysis of a dwarf and deformed flower3 (ddf3) mutant in rice (*Oryza sativa* L.) and characterization of candidate genes". Journal of Integrative Agriculture. 17(5): 1057-1065. (Year: 2018).*

Fan et al. "GS3, a major QTL for grain length and weight and minor QTL for grain width and thickness in rice, encodes a putative transmembrane protein". Theoretical and Applied Genetics. 112: 1164-1171. (Year: 2006).*

Olson, S. "The third generation of hybrid rice: unlocking the possibilities of chloroplast transformation". The World Food Prize Foundation. China National Hybrid Rice Research and Development Center. (Year: 2014).*

Fincher, G.B., and Johnson, C. "A cereal chemist's quick guide to genetics, plant breeding and BioIT". Australian Centre for Plant Functional Genomics, University of Adelaide. 2005 (Year: 2005).*

Xu, Erbo et al., Application of Small Grain Recessive Gene in the Mechanical Sorting of Hybrid Rice Seeds,China Rice, 2015, pp. 8-11, vol. 21(3).

* cited by examiner

METHOD FOR BREEDING SMALL-GRAIN STERILE RICE LINE AND SIMPLE METHOD FOR PRODUCING HYBRID RICE SEED

CROSS REFERENCE TO THE RELATED APPLICATIONS

This application is the national phase entry of International Application No. PCT/CN2017/093249, filed on Jul. 18, 2017, which is based upon and claims priority to Chinese Patent Application No. 201610679340.0, filed on Aug. 17, 2016, the entire contents of which are incorporated herein by reference.

TECHNICAL FIELD

The present disclosure relates to the field of rice seed production, and more specifically relates to a method for breeding a small-grain male sterile rice line. Moreover, the present disclosure further relates to a simple method for producing a hybrid rice seed.

BACKGROUND

Successful breeding and the widespread use of hybrid rice have played an important role in promoting stable food production and ensuring China's food security. Traditional hybrid rice seed production requires respectively seeding, transplanting, and managing parental lines in different fields to achieve an ideal state with the same flowering time. This method includes manual pollination, separation and harvesting of the parental lines, which is complicated, labor-intensive, and costly. In recent years, with the development of China's socio-economic and urbanization, agricultural labor has become increasingly scarce, making this labor-intensive cultivation method for hybrid rice seed production increasingly difficult to implement. The difficulty to implement labor intensive cultivation methods will seriously affect the safe production and supply of hybrid rice seeds. It is therefore urgent to achieve a simple, efficient method for large-scale hybrid rice seed production by an integration of current research. The implementation of current research can greatly reduce labor input and labor intensity and improve work efficiency, thereby ensuring the safe, efficient production and supply of hybrid rice seeds, and maintaining China's international leading position in the field of hybrid rice techniques.

At present, mechanized operations have been partially realized in the research of hybrid rice mechanized seed production techniques. In the field management of the parental lines, American RiceTec Inc., Germany Bayer Co., Ltd., and others, employ seed production techniques such as mechanical dry drill-seeding and harvesting, mechanical or agricultural aircraft spraying and fertilization, and helicopter crop dusting to achieve large-scale semi-mechanized seed production. South Korea and Japan have basically realized mechanization in ploughing, crop protection, harvesting, drying and other operations in 1980's and 1990's, respectively. In China, mechanical operations have been realized in the operations of land plowing, mechanical dry drill-seeding and rice transplanting of parental lines, pesticide and gibberellin spraying, harvesting, drying, etc. Currently, the optimal combination of parental lines with the same duration from seeding to heading (DSH) is researched abroad. There were significant differences in grain color, grain weight or grain shape between a female parent and a male parent. For example, hybrid rice mechanized seed production may be realized by using the techniques of parental line mixed sowing and harvesting when the small rice grain male sterile line is used for seed production, however, the progress of this research has not been achieved. The key to the parental line mixed planting seed production technique in hybrid rice planting mechanization, is the achievement of the seed mechanized sorting of parental line seeds. So far, due to the limitation of sterile lines, no suitable mechanized sorting method has been put in production.

SUMMARY

The present disclosure provides a method for breeding a small-grain male-sterile rice line and a simple method for producing a hybrid rice seed, so as to solve the technical problem of parental line mixed sowing and harvesting during seed production.

The technical scheme in the present invention is as follows:

One aspect of the present invention, a method for breeding a small-grain sterile rice line is provided, including the following steps:

Crossing a female parent C815S with a male parent Qigui B to obtain a hybrid seed F1; planting the F1 and crossing the F1 with a female parent H155S to obtain a crossed hybrid seed F1'; planting the crossed hybrid seed F1' to obtain a F2' generation; planting an individual plant with ideal plant type, strong tillering, plant dwarf and small grain types from the F2'-generation and a F3' generation, and then directional breeding, more than two generations, to obtain a seed with more than F5' generation as the small-grain sterile rice line.

Further, in the breeding process, generations from the F1' generation are selected under a short-day low-temperature stress condition and a long-day low-temperature stress condition, provided alternately from generation to generation; wherein the short-day low-temperature stress condition includes a light period of less than 12 hours, and an average daily temperature of less than 23° C.; and the long-day low-temperature stress condition includes a light period of greater than 12 hours, and an average daily temperature of less than 23° C.

Further, the small-grain sterile rice line are the seeds of the F5' to F9' generation. Further, the small-grain sterile rice line has a 1000-grain weight of 8-22 g and a grain thickness of less than 2.1 mm.

In another aspect of the present invention, a simple method for producing a hybrid rice seed is provided, including the following steps:

A large-grain restorer rice line as a male parent, and the above-small-grain male sterile line as a female parent are formed as a hybrid combination and direct-seeded simultaneously.

Both the male parent and the female parent are mixed and harvested simultaneously.

According to the difference in grain thickness, the male parental seed and the female parental seed are obtained by screening and separating, and the female parental seed is the hybrid seed.

Alternatively, the large-grain restorer rice line is one selected from the group consisting of R9311, Wanghui 780, Xinhui 1998, and Wanghui 091.

Wanghui 780 is obtained through breeding. The breeding process includes the following steps:

Crossing R9311 with Shuhui 498 to obtain a hybrid seed F1", breeding the F1" and F2", and mixed harvesting, and screening seeds with a 1000-grain weight of greater than 30 g, a grain thickness of greater than 2.2 mm, and good rice quality from generations from F3" to F5" for planting to obtain the next generation. Seeds of equal to or more than F6" generation are the large-grain restorer rice line.

Optionally, the large-grain restorer rice line has a 1000-grain weight of more than 30 g and a grain thickness of equal to or more than 2.2 mm.

Optionally, the manner of seeding the male parent and the female parent includes a manner of seeding a sprouting rice as the male parent and a dry rice as the female parent, a manner of seeding a dry rice as the male parent, and a sprouting rice as the female parent, a manner of seeding a first sprouting rice as the male parent, and a second sprouting rice as the female parent, or a manner of seeding a first dry rice as the male parent, and a second dry rice as the female parent.

Among them, when the manner is seeding a sprouting rice as the male parent and a dry rice as the female parent, the ratio of the male parent sprouting rice to the female parent dry rice is 1:1.

Optionally, the manner of the direct-seeding is one selected from the group, consisting of a manner of mixed direct-seeding of the male parent and the female parent, a manner of drill direct-seeding the male parent and the female parent, and the manner of seedling-throwing the male parent and direct-seeding the female parent.

Optionally, the pore size of the screen is 2.1 mm wide and 20 mm long.

The present invention has the following advantages: the above method for breeding the small-grain male sterile rice line uses C815S as the female parent and Qigui B as the male parent to obtain the hybrid seed F1, and the F1 is crossed with H155S as the female parent to obtain the hybrid seed F1'. A directional cultivation is per-mannered to obtain the small-grain male sterile line. The small-grain male sterile line prepared by the above male sterile line breeding method has the advantages of a high seed-setting rate, high germination and seedling rate, strong storage resistance, and low kernel smut rate.

In addition to the objectives, features, and advantages described above, the present invention has other objectives, features, and advantages. Hereinafter, the present invention is described in further detail with reference to the drawings.

BRIEF DESCRIPTION OF THE DRAWINGS

The drawings in the present disclosure are used to help a further understanding of the present invention. The schematic embodiments of the present disclosure and the descriptions thereof are used to explain the present invention, and should not be regarded as an improper limitation on the present invention. In the drawings.

DETAILED DESCRIPTION OF THE EMBODIMENTS

The embodiments of the present invention are described in detail with references to the drawings above. The present invention can be implemented in various ways that are covered by the claims.

Figure 1:
FIG. 1 is a diagram showing a comparison of the Zhuo 201S and Wanghui 091 in grain shape according to a preferred embodiment of the present invention.

Referring to FIG. 1, a preferred embodiment of the present invention provides a method for breeding a small-grain sterile rice line is provided, including the following steps.

A female parent C815S is crossed with a male parent Qigui B to obtain a hybrid seed F1. The F1 is planted and crossed with a female parent H155S to obtain a crossed hybrid seed F1'. The crossed hybrid seed F1' is planted to obtain a F2' generation. An individual plant with ideal plant type, strong tillering, plant dwarf and small grain type from the F2'-generation and a F3' generation is planted, followed by directional breeding more than two generations to obtain a seed with more than F5' generation as the small-grain sterile rice line.

The present invention has the following advantage: the above method for breeding the small-grain male sterile rice line uses C815S as the female parent and Qigui B as the male parent to obtain the hybrid seed F1, and the F1 is crossed with H155S as the female parent to obtain the hybrid seed F1'. A directional cultivation is pre-mannered to obtain the small-grain male sterile line. The small-grain male sterile line prepared by the above male sterile line breeding method has the advantages of high outcrossing seed-setting rate, high germination and seedling rate, strong storage resistance, and low kernel smut rate.

Optionally, in the breeding process, generations from the F1' generation are selected under a short-day low-temperature stress condition and a long-day low-temperature stress condition provided alternately from generation to generation. Wherein the short-day low-temperature stress condition includes a light period of less than 12 hours, and an average daily temperature of less than 23° C., and the long-day low-temperature stress condition includes a light period of greater than 12 hours, and an average daily temperature of less than 23° C.

The short-day low-temperature condition and the long-day low-temperature condition can be achieved by selecting an appropriate breeding base and breeding season. For example, the city Hainan has a short day and a low temperature, the city Changsha has a long day and a low temperature in summer, and a short day and a low temperature in autumn. Further, the indoor experimental environment can also be adjusted by experimental equipment.

Take the mannered method as an example. In the summer of 2011, H155S was used as the female parent, and the F1 obtained by crossing the two-line male sterile line C815S with Qigui B was used as the male parent. Through stress selections under the short-day low temperature condition in Hainan, the short-day low-temperature condition in Changsha in autumn, a stress-increasing fertility selection in human-controlled water temperature ponds, the small-grain dual-use nuclear male sterile line Zhuo 201S with high quality, ideal plant type, and low critical temperature of sterility was obtained in 2016 after a selective cultivation of 9 generations in 5 years. The Zhuo 201S was deposited at the China Center for Type Culture Collection (CCTCC) with a Latin name of *Oryza sativa* L. Zhuo 201S, a deposit date of Aug. 12, 2016, and a deposit number of CCTCC NO: P201615.

According to the fertility conversion characteristics of the dual-use nuclear male sterile line between Hainan province and Hunan province, a shuttle breeding was pre-mannered under a short-day low-temperature condition and a long-day low-temperature condition, ensuring that the cultivated low temperature induced male sterile line had a stable fertility transamination property under relatively complicated ecological conditions.

The male sterile line selected under the short-day low-temperature condition in Sanya, Hainan in February and March have a lower critical temperature of sterility and even a harder breeding under the long-day condition in Hunan, possessing an interdynamic relationship between light and temperature.

Further, the small-grain sterile rice line is the seed of the F5' to F9' generation. Further, the small-grain sterile rice line has a 1000-grain weight of 8-22 g and a grain thickness of less than 2.1 mm.

In another aspect of the present invention, a simple method for producing a hybrid rice seed is provided, including the following steps.

A large-grain restorer rice line as a male parent, and the above small-grain male sterile line as a female parent are formed as a hybrid combination and direct-seeded simultaneously.

Both the male parent and the female parent are simultaneously mixed harvested.

According to the difference in grain thickness, the male parental seed and the female parental seed are obtained by screening and separating, and the female parental seed is the hybrid seed.

The hybrid seeds produced by the small-grain sterile rice line and the large-grain restorer rice line are controlled by the genotype of the female parent, i.e., the small-grain sterile rice line, and are small grained. The male parent seeds are controlled by the genotype of the large-grain restorer rice line and are large-grained. If the 1000-grain weight of the male parent restorer line is equal to, or more than 26 g, it can be planted by mixed sowing or drill seeding and can at least be mixed when harvested (male parent and female parent), especially mechanized mixed harvesting. The harvested mixed seeds are sorted through a suitable mesh screen to separate the hybrid seeds from the male parent seeds. The principle is that when the hybrid seeds are cleaned through the mesh screen, small seeds (hybrid seeds on the female parent) with a grain thickness of less than 2.1 mm pass through the mesh screen, while normal and large seeds cannot pass through the mesh screen, thereby achieving the separation. Specifically, the sorting may be done manually or mechanically. Because the small grain is controlled by a single recessive gene, a large grain is obtained by sowing the hybrid seed, without affecting the production and expression of the hybrid rice.

Small-grain male sterile rice lines are used for seed production and combined with large-grain restorer rice lines with a large grain size and suitable growth period, and the male and female parents are direct-seeded simultaneously, which simplifies the seed production, eliminates seedling and transplanting, saves labor, and simplifies the pollination process (or does not require auxiliary pollination). The male and female parents can be mixed harvested. After the male and female parents have raised flowers, there is no need to harvest the female parent separately. Instead, the male and female parents can be mixed and harvested by a harvesting machine, which reduces production costs.

The mixed male parent seeds and the hybrid seeds after harvesting are separated with the mesh screen due to their different 1000-grain weight, i.e., different grain sizes. By designing different sizes of the mesh screen, the small-grain hybrid seeds generated on the small-grain sterile rice lines can be separated from the large-grain or normal restorer lines. In the present disclosure, a small-grain male sterile rice line and a large-grain restorer rice line with similar DSH, and large grain size differences, are selected for breeding, and the difference of grain thickness is used in screening. For example, sorting machinery modification techniques may be used to design a specific mesh screen to sort the male and female parents mechanically, thereby realizing the full mechanization of seed production.

In particular, the 1000-grain weight of the small-grain sterile rice line Zhuo 201S, which was bred during the breeding process of the small-grain sterile rice line, was 14.6 g, while the 1000-grain weight of the current restorer rice line is generally above 25 g. Therefore, the small-grain sterile rice line Zhuo 201S has a larger difference and is easier to separate, which can ensure the purity of hybrid seeds.

In addition, the use of small-grain sterile rice lines for seed production, on the one hand, can increase the breeding coefficient of hybrid seeds, which not only saves rice fields for the seed production, but also reduces the cost for farmers to purchase hybrid rice seeds. On the other hand, it can reduce labor input, simplify seed production procedures, and reduce production costs. The small-grain combination is also an effective way to improve the quality of hybrid rice. Small-grain seeds have a relatively short grain filling period and good filling, which can effectively reduce the occurrence of chalkiness. Especially in the high-temperature, high-humidity climate during the grain filling stage of early indica rice in southern China, this advantage of the small-grain seeds is extremely obvious.

Moreover, in the simple method for producing the hybrid rice seed in the present disclosure, the outcrossing seed-setting rate was 21.7% higher than that of Y58S, and the seed production yield was 18.6% higher than that of the Y58S. The germination potential and seedling rate of the hybrid seed were high. With the same male parent, the germination potential and seedling rate were 6.9% and 7.3% higher than those of the Y58S, respectively. The hybrid seed has strong storage resistance. When stored at room temperature for one year, the seedling rate reached 87.4%, which was 33.9% higher than that of the Y58S. The hybrid seed had less kernel smut infection, and the rate of the kernel smut infection was 77.6% less than that of the Y58S. The Y58S is a variety bred by Hunan Hybrid Rice Research Center and has applied for protection of new plant variety rights.

Optionally, the large-grain restorer rice line is one selected from the group consisting of R9311, Wanghui 780, Xinhui 1998, and Wanghui 091. The Wanghui 780 was deposited at the China Center for Type Culture Collection (CCTCC) with a Latin name of *Oryza sativa* L. Wanghui 780, a deposit date of Aug. 12, 2016, and a deposit number of CCTCC NO:P201616. The Wanghui 780 is obtained through breeding. The breeding process includes the following steps: crossing R9311 with Shuhui 498 to obtain a hybrid seed F1", breeding the F1 "and F2", and mixed harvesting, and screening seeds with a 1000-grain weight of greater than 30 g, a grain thickness of greater than 2.2 mm, and good rice quality from generations from F3" to F5" for planting to obtain a next generation. Seeds of equal to, or more than, F6"generation are the large-grain restorer rice line. The finally obtained Wanghui 780 has a large 1000-grain weight, reaching about 34 g, a grain thickness of more than 2.3 mm, and good rice quality and strong combining ability.

R9311, namely Yangdao 6, is a conventional indica rice variety developed by the Agricultural Research Institute of Lixiahe District, Jiangsu, which passed the Shaanxi Provincial Examination in 2003 as Shaanxi Examined Rice 2003001, and is a commercially available product. Xinhui 1998 and Wanghui 091 were developed by Hunan Hope Seed Industry Technology Co., Ltd. and have applied for the protection of new plant variety rights. Mixed harvesting means that no screening is pre-mannered, all seeds obtained from F1 "are planted, and all seeds obtained from F2" are planted as well.

Optionally, the large-grain restorer rice line has a 1000-grain weight of more than 30 g and a grain thickness of equal to or more than 2.2 mm.

Optionally, the manner of seeding the male parent and the female parent includes a manner of seeding a sprouting rice as the male parent and a dry rice as the female parent, a manner of seeding a dry rice as the male parent and a sprouting rice as the female parent, a manner of seeding a first sprouting rice as the male parent and a second sprouting rice as the female parent, or a manner of seeding a first dry rice as the male parent and a second dry rice as the female parent. Among them, when the manner is seeding a sprouting rice as the male parent and a dry rice as the female parent, the ratio of the male parent sprouting rice to the female parent dry rice is 1:1.

Figure 2:
FIG. 2 is a diagram showing Zhuo 201S and Wanghui 780 at a seedling stage by mixed direct-seeding for producing seeds according to a preferred embodiment of the present invention.
Figure 3:
FIG. 3 is a diagram showing Zhuo 201S and Xinhui 1998 at a seedling stage by drill seeding for producing seeds according to a preferred embodiment of the present invention.

Optionally, the manner of the direct-seeding is one selected from the group consisting of a manner of mixed direct-seeding the male parent and the female parent, a manner of drill direct-seeding the male parent and the female parent, and a manner of seedling-throwing the male parent, and direct-seeding the female parent. When the male parent is similar to the female parent in DSH, the seeding can be carried out by any of the manners described above. When the male parent is largely different from the female parent in DSH, it is preferred to use the manner of drill direct seeding the male parent and the female parent. Generally, the DSH of the male parent is relatively long, and the flowering period of the male parent can be adjusted by spraying "920" (gibberellic acid) on the male father or another method, allowing the male parent to have a flower synchronization with the female parent. For other seeding manners, it is obviously inconvenient to operate, which is not conducive to adjusting the flowering period of the male parent. As shown in FIG. 2, at the seedling stage of the small-grain male sterile line Zhuo 201S and the large-grain restorer rice line Wanghui 780 that were mixed direct-seeded for seeds. The male and female parents both grew normally and vigorously. The female parent grew around the male parent, which was easy to receive pollen. As shown in FIG. 3, at the seedling stage of the Zhuo 201S and the Xinhui 1998 that were drill direct-seeded for seeds. The male and female parents both grew neatly, and the quality by the drill direct seeding was good.

Optionally, the pore size of the screen is 2.1 mm wide and 20 mm long. The screen with the pore size can effectively screen and separate the male paternal seeds from the female parental seeds.

Embodiment 1

A selection process for breeding a small-grain sterile line is as follows.

In the summer of 2011, H155S was used as the female parent, and the F1 obtained by crossing the two-line male sterile line C815S with Qigui B was used as the male parent. Through stress selections under the short-day low temperature condition in Hainan, the short-day low-temperature condition in Changsha in autumn, a stress-increasing fertility selection in human-controlled water temperature ponds, the small-grain dual-use nuclear male sterile line Zhuo 201S with high quality, ideal plant type, and low critical temperature of sterility, was obtained in 2016 after a selective cultivation of 9 generations in 5 years. The selection process is shown in Table 1.

TABLE 1

Selection process chart of Zhuo 201S

| Year and Seasons | Location | Generation | Generation Description |
|---|---|---|---|
| 2011, Summer | Changsha | F0' | C815S and Qigui B were crossed and 18 seeds were harvested. |
| 2011, Winter | Hainan | F0' | The F1 obtained by crossing C815S with Qigui B is planted, in total 14 plants. At head sprouting stage, H155S as the female parent was crossed with F1 obtained by crossing C815S with Qigui B as the male parent, and 217 seeds were harvested. |
| 2011, Summer and Autumn | Changsha | F1' | 164 plants were planted. 20 hybrid plants were selected for mixed harvesting. |
| 2012, Winter | Hainan | F2' | 2500 plants were planted. The individual plants with ideal plant type, strong tillering, plant dwarf and small grain type were selected for mixed harvesting. 0.25 kg of seeds were obtained. |
| 2013, Summer and Autumn | Changsha | F3' | 2100 plants were planted. The plants with ideal plant type, strong tillering, and plant dwarf were selected for bagging and the individual plants with small grain type were selected for reproducing after cutting. 0.25 kg of seeds were obtained. |
| 2014, Winter | Hainan | F4' | 3500 rows were planted. The plants with ideal plant type, strong tillering, and plant dwarf were selected for bagging and 211 individual plants with small grain type were selected. |

TABLE 1-continued

Selection process chart of Zhuo 201S

| Year and Seasons | Location | Generation | Generation Description |
|---|---|---|---|
| 2014, Summer and Autumn | Changsha and Baoshan, Yunnan | F5' | Each of the 211 materials was divided into two parts and planted in Baoshan of Yunnan, and Chating of Wangcheng in Changsha, respectively. Fertility, morphology, and resistance selections were performed in Changsha. Among them, the 201 plant showed outstanding performance in Changsha, which was in line with breeding goals, and the agronomic traits were basically stable. In Baoshan of Yunnan, the 201 plant showed a good resistance and good reproducibility, and was subjected to isolation and expansion to continue for purification. The selected plants were cut off at stump and regenerated, brought to Hainan with their stumps, and were isolated and reproduced in row. |
| 2014, Winter | Hainan | F6' | The purification, isolation and propagation were continued, and a small number were subjected to a hybrid test. |
| 2015, Summer and Autumn | Changsha, and Baoshan, Yunnan | F7' | Each of the materials was divided into two parts and planted in Baoshan of Yunnan, and Chating of Wangcheng in Changsha, respectively. The desired lines were determined in Changsha and the seeds thereof were harvested in Baoshan. A small amount of seed production was carried out and the combination advantages were identified. |
| 2015, Winter | Hainan | | Observation of characteristics, analysis of combining ability, stress-increasing fertility selection, hybrid test, etc. were performed. A site preparation for identifying the 201S in Hainan was done, and the simple method for producing the seed was tested. |
| 2016-To date | Changsha | | Research on stress-increasing fertility selection, combination for hybrid test, light and temperature characteristics, fertility conversion, breeding and feed production techniques, etc., were further performed. Fertility identification, and combination regional trials were carried out. |

III. Characteristics

1. Fertility Performance

Referring to Table 2, Zhuo 201S showed male sterility in heading and flowering from the end of June or the beginning of July to the end of August. In Sanya, Hainan, the Zhuo 201S showed the male sterility in heading and flowering at around the end of March showed male sterility. When the Zhuo 201S was treated with a constant temperature of 23.0° C., 23.5° C., and 24.0° C. for 5 days (Table 3), respectively, the fertile pollen rates were all zero, indicating that the critical temperature of sterility of the Zhuo 201S is less than 23.0° C. The identification results of the pollen fertility of the Zhuo 201S are shown in Table 3.

TABLE 2

Fertility performance of Zhuo 201S in identification tests of ecological adaptability in Hunan and Hainan

| Location | Year | Sterile phase/ (Month-Day) | Sterile period/d | Fertility fluctuating phase/ (Month-Day) | Mean low temperature in Fertility fluctuating phase/° C. | Low temperature duration Fertility fluctuating phase/d | Staining pollen rate/% |
|---|---|---|---|---|---|---|---|
| Changsha | 2014 | 06-25~08-28 | 64 | 08-28~31 | 23.3 | 3 | 0.3 |
| | 2015 | 06-28~08-30 | 63 | 06-28 | 21.9 | 3 | 26.6 |
| | | | | 08-30~09-04 | 22.17 | 3 | 1.9 |
| Haikou | 2014 | 03-28~04-05 | 86 | 03-28~4-05 | 22.8 | 4 | 1.5 |
| | 2015 | 03-25~04-05 | 68 | 03-25 | 22.64 | 5 | 2.8 |
| | | | | 04-05 | 23.2 | 2 | 1.7 |
| | | | | 03-05 | 21.4 | 2 | 9.8 |
| Sanya | 2014 | 03-05~03-20 | 87 | 03-20 | 21.56 | 3 | 35.3 |
| | 2015 | 03-08~03-15 | 87 | 03-08 | 21.1 | 5 | 66.7 |
| | | | | 03-15 | 21.67 | 6 | 66.5 |

TABLE 3

Identification results of pollen fertility of
dual-use nuclear male sterility line Zhuo 201S

| Light length | Temperature | Number of plants | Number of rice panicles inspected | Pollen kernel smut infection rate Mean | Pollen infection rate Mean | Pollen infection rate Maximum | Pollen infection rate Minimum |
|---|---|---|---|---|---|---|---|
| 13.5 h | 23.0° C. | 9 | 18 | 0.000% | 0.000% | 0.000% | 0.000% |
| | 23.5° C. | 9 | 18 | 0.000% | 0.000% | 0.000% | 0.000% |
| | 24.0° C. | 9 | 18 | 0.000% | 0.000% | 0.000% | 0.000% |

2. Fertility characteristics

The Zhuo 201S was planted as early season rice in Sanya. It was sown on January 28 and was transplanted around February 28. The heading started around April 24 and the DSH lasted about 84 days. The Zhuo 201S was planted as early season rice in Changsha, It was sown on May 26, and was transplanted around June 12. The full heading started before August 13, and the DSH lasted about 79 days.

3. Morphological Characteristics and Agronomic Traits

Zhuo 201S has a plant height of about 70 cm and a compact-moderate plant profile. The early leaves are droopy, and the latter three leaves are relatively upright. The flag leaves are 25 cm long and 1.5 cm wide with an included angle of about 45° C. The leaf color is light green. The leaf sheaths and apiculus are colorless. The stem is of medium thickness and strong tillering. Generally, each plant has 17-19 effective panicles with an average of 15 mature panicles. The length of the panicles is about 28 cm. The average number of panicleletes per panicle is about 178. The grain has a length of 6.4 mm and the grain aspect ratio is 3.3:1. The grain are full with a 1000-grain weigh of about 14.6 g.

4. Outcrossing Characteristics

Zhuo 201S has a good outcrossing characteristic. The panicle is large with a slightly curved shape when flowering and a flowering period of 4-5 days. The flowering time is early. The flowering period is from 10:30 to 12:00. The peak of flowering is obvious. Flowers account for more than 75% before noon. The flower synchronization probability during flowering is high. The panicle enclosure rate is about 10%, and the stigma exposure rate is high. Without spraying "920", the total stigma exposure rate is 88.2%, where the bilateral exposure rate is 62.2%. The stigma viability is strong. The outcrossing seed setting rate can reach about 80%. The seed production is easy with a high yield. The Zhuo 201S is relatively sensitive to "920". When heading 15-20%, spraying 15 g of "920" per mu (about 667 square meters) can avoid panicle enclosure.

5. Rice Quality

In the winter of 2015, Zhuo 201S rice, which was propagated in Haitangwan Town, Sanya, Hainan, was analyzed, showing that the brown rice rate was 80.3%, the polished rice rate was 71.8%, the whole polished rice rate was 59.1%, the grain length was 6.1 mm, the grain aspect ratio was 3.3:1, the chalky rice rate was 11.0. %, the chalkiness degree was 1.0%, the transparency was 1 grade, the alkali elimination value was 6.0, gel consistency was 65 mm, the amylose content was 15.8%, and the protein content was 9.5%.

6. Zhuo 201S Resistance

Zhuo 201S was identified by Liuyang Dawei Mountain Rice Blast Identification Base in 2015, showing that the seedling blast was grade 3, the panicle blast was grade 5, the comprehensive rating was 3.1; the bacterial blight resistance was grade 5 and the sheath blight was mild.

7. Grain Shape of Zhuo 201S

The grain shape comparison between Zhuo 201S and Wanghui 091 is shown in FIG. 1, where the small grain is Zhuo 201S and the large grain is the restorer line Wanghui 091 developed by Hunan Hope Seed Industry Technology Co., Ltd. It can be seen that there is a significant difference in thickness between the Zhuo 201S and Wanghui 091, which is conducive to the separation of male paternal seeds and female paternal seeds.

Embodiment 2

Figure 4:
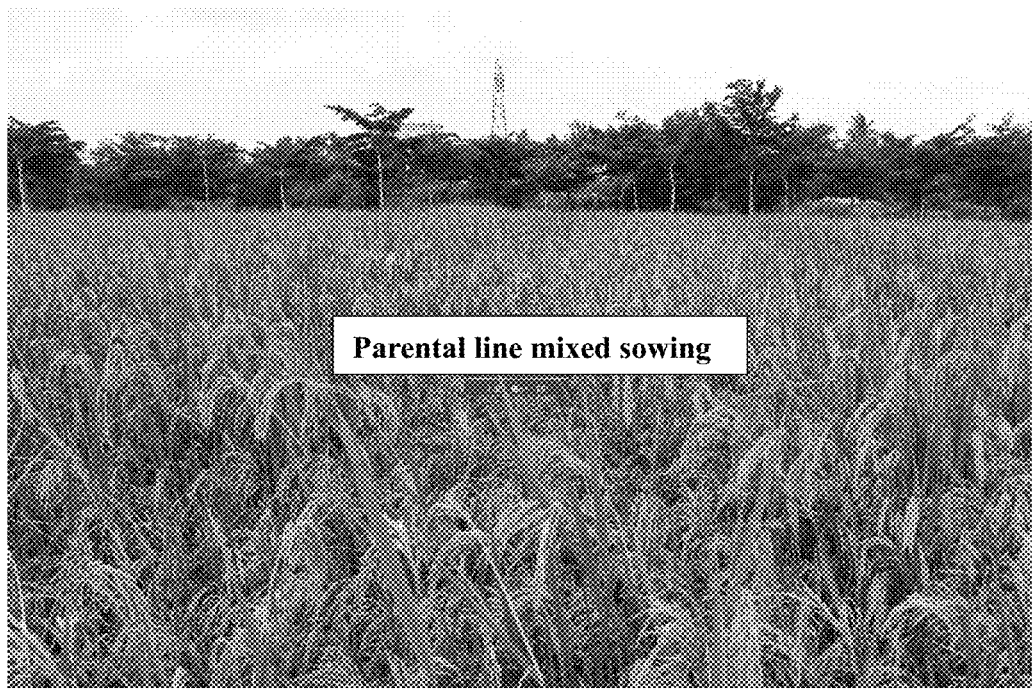
FIG. 4 is a diagram showing Zhuo 201S and Wanghui 780 at a mature stage by mixed direct-seeding for producing seeds according to a preferred embodiment of the present invention.

In April 2016, a hybrid seed production was performed in Haitang Bay, Sanya, Hainan, where the large-grain male parent Wanghui 780 was used as the male parent, and Zhuo 201S was used as the female parent. The male and female parents were mixed sown at the same time on January 25 with the ratio of the male parent to the female parent of 1:20, and the ratio of male parent dry rice to the female parent sprouting rice of 1:1. The male and female parents started heading at the same time on April 18. The male and female parents were mixed and applied "920" at 15 g/mu at the same time on April 20. Artificial auxiliary pollination was performed once only when it was in a windless state. They matured on May 20. As shown in FIG. 4, in the mature stage by mixed direct-seeding the Zhuo 201S and Wanghui 780 for producing seeds, the male parent space occupied a small space and had a small proportion. The seed breeding rate was high. They were mixed harvested on May 20. Under the condition that the pore size of the screen was 2.1 mm wide and 20 mm long, mechanical screening is performed to successfully separate to obtain the male parental seeds and female parental seeds. The purity of the female parental seeds, i.e., hybrid seeds, was 99.76%.

While Zhuo 201S was used as the female parent for seed production, Y58S was used as the female parent for control experiments under the same conditions. The outcrossing seed setting rate and seed production yield of the group with the Zhuo 201S as the female parent and the group with the Y58S as the female parent were obtained by statistics. Then, the hybrid seeds obtained from each group were planted separately, and the germination potential, seedling rate, seed cracking rate and kernel smut infection rate of each group of hybrid seeds were obtained by statistics. The statistical results of the relevant data of each group are shown in Table 4:

TABLE 4

Results of simple seed production of male sterile lines and Wanghui 780

| Male sterile lines | Outcrossing seed setting rate/% | Seed production yield/ kg · mu$^{-1}$ | Germination potential/% | Seedling rate/% | Seed cracking rate/% | Kernel smut infection rate/% |
|---|---|---|---|---|---|---|
| Zhuo 201S | 81.4 | 269.3 | 92.4 | 89.6 | 1.47 | 0.0 |
| Y58S | 59.7 | 219.2 | 86.0 | 83.1 | 9.7 | 13.64 |
| Advantage | 21.7 | 18.6 | 6.9 | 7.3 | −8.23 | −13.64 |

Under the same conditions, the outcrossing seed setting rate of the Zhuo 201S group was 21.7% higher than that of the Y58S group, and the seed production yield was 18.6% higher than that of the Y58S group. The hybrid seeds produced by the Zhuo 201S group had high germination potential and seedling growth rate, with 6.9% and 7.3% higher than those of the Y58S group, respectively. The seed cracking rate of the hybrid seeds produced by the Zhuo 201S group was 1.47%, which was 8.23% less than that of the Y58S group. The hybrid seeds produced by the Zhuo 201S group were not infected with kernel smut, while the kernel smut infection rate of the Y58S group was 13.64%.

Embodiment 3

In April 2016, a hybrid seed production was performed in Haitang Bay, Sanya, Hainan, where the large-grain male parent Wanghui 091 was used as the male parent, Zhuo 201S was used as the female parent, and N111S was used as a female parental control. The male and female parents were mixed sown at the same time on January 25 with the ratio of the male parent to the female parent of 1:20, and the ratio of male parent dry rice to the female parent sprouting rice of 1:1. The male and female parents started heading at the same time on April 18. The male and female parents were mixed applied "920" at 15 g/mu at the same time on April 20. Artificial auxiliary pollination was performed once only when it was in a windless state. They matured on May 20. Under the condition that the pore size of the screen was 2.1 mm wide and 20 mm long, mechanical screening is performed to successfully separate to obtain the male parental seeds and female parental seeds. The purity of the female parental seeds, i.e., hybrid seeds, was 99.51%.

Figure 5:
FIG. 5 is a diagram showing a comparison of Zhuo 201S and N111S with Wanghui 091 respectively at a mature stage in seed production according to the preferred embodiment of the present invention.

While Zhuo 201S was used as the female parent for seed production, N111S was used as the female parent for control experiments under the same conditions. The outcrossing seed setting rate and seed production yield of the group with the Zhuo 201S as the female parent and the group with the N111S as the female parent were obtained by statistics. As shown in FIG. 5, on the left side is the group with the Zhuo 201S as the female parent. Then, the hybrid seeds obtained from each group were planted separately, and the germination potential, seedling rate, seed cracking rate and kernel smut infection rate of each group of hybrid seeds were obtained by statistics. The statistical results of the relevant data of each group are shown in Table 5:

TABLE 5

Results of simple seed production of male sterile lines and Wanghui 091

| Male sterile lines | Outcrossing seed setting rate/% | Seed production yield/ kg · mu$^{-1}$ | Germination potential/% | Seedling rate/% | Seed cracking rate/% | Kernel smut infection rate/% |
|---|---|---|---|---|---|---|
| Zhuo 201S | 80.2 | 255.7 | 90.5 | 88.2 | 2.54 | 0.0 |
| N111S | 29.7 | 119.2 | 81.0 | 75.1 | 35.6 | 15.12 |
| Advantage | 58.5 | 53.3 | 9.5 | 13.1 | −33.06 | −15.12 |

Under the same conditions, the outcrossing seed setting rate of the Zhuo 201S group was 58.5% higher than that of the N111S group, and the seed production yield was 53.3% higher than that of the N111S group. The hybrid seeds produced by the Zhuo 201S group had high germination potential and seedling growth rate, with 9.5% and 13.1% higher than those of the N111S group, respectively. The seed cracking rate of the hybrid seeds produced by the Zhuo 201S group was 2.54%, which was 33.06% less than that of the Y58S group. The hybrid seeds produced by the Zhuo 201S group were not infected with kernel smut, while the kernel smut infection rate of the N111S group was 15.12%.

Embodiment 4

In April 2016, a hybrid seed production was performed in Haitang Bay, Sanya, Hainan, where the large-grain male parent Xinhui 1998 was used as the male parent, and Zhuo 201S was used as the female parent. The male and female parents were mixed sown at the same time on January 25 with the ratio of the male parent to the female parent of 1:20, and the ratio of male parent dry rice to the female parent sprouting rice of 1:1. The male and female parents started heading at the same time on April 18. The male and female parents were mixed and applied "920" at 15 g/mu at the same time on April 20. Artificial auxiliary pollination was performed once only when it was in a windless state. They matured on May 20. Under the condition that the pore size of the screen was 2.1 mm wide and 20 mm long, mechanical screening is performed to successfully separate to obtain the male parental seeds and female parental seeds. The purity of the female parental seeds, i.e., hybrid seeds, was 99.05%.

While Zhuo 201S was used as the female parent for seed production, Y58S was used as the female parent for control experiments under the same conditions. The outcrossing seed setting rate and seed production yield of the group with the Zhuo 201S as the female parent and the group with the Y58S as the female parent were obtained by statistics. Then, the hybrid seeds obtained from each group were planted separately, and the germination potential, seedling rate, seed cracking rate and kernel smut infection rate of each group of hybrid seeds were obtained by statistics. The statistical results of the relevant data of each group are shown in Table 6:

TABLE 6

Results of simple seed production of male sterile lines and Xinhui 1998

| Male sterile lines | Outcrossing seed setting rate/% | Seed production yield/ kg · mu$^{-1}$ | Germination potential/% | Seedling rate/% | Seed cracking rate/% | Kernel smut infection rate/% |
|---|---|---|---|---|---|---|
| Zhuo 201S | 78.9 | 231.6 | 93.2 | 87.6 | 1.15 | 0.0 |
| Y58S | 61.3 | 207.2 | 87.4 | 82.2 | 11.7 | 8.26 |
| Advantage | 17.6 | 11.5 | 5.8 | 5.4 | −10.55 | −8.26 |

Under the same conditions, the outcrossing seed setting rate of the Zhuo 201S group was 17.6% higher than that of the Y58S group, and the seed production yield was 11.5% higher than that of the Y58S group. The hybrid seeds produced by the Zhuo 201S group had high germination potential and seedling growth rate, with 5.8% and 5.4% higher than those of the Y58S group, respectively. The seed cracking rate of the hybrid seeds produced by the Zhuo 201S group was 1.15%, which was 10.55% less than that of the Y58S group. The hybrid seeds produced by the Zhuo 201S group were not infected with kernel smut, while the kernel smut infection rate of the Y58S group was 8.26%.

Comprehensively comparing embodiments 2-4, the hybrid seeds obtained by using the Zhuo 201S as the female parent and the Wanghui 780 as the male parent had the highest outcrossing seed setting rate, the highest seed production yield, the highest seedling rate. Only the germination potential and seed cracking rate were slightly lower than those in embodiment 4. In addition, the DSH of the Zhuo 201S as the female parent is close to that of the Wang Hui 780. Under comprehensive comparison, embodiment 2 is the preferred embodiment.

The above descriptions are merely preferred embodiments of the present invention and are not intended to limit the present invention. For those skilled in the art, the present invention may have various modifications and changes. Any modification, equivalent replacement, or improvement made within the spirit and principle of the present invention shall fall in the protection scope of the present invention.

What is claimed is:

1. A method for producing a hybrid rice seed, comprising the following steps:
   simultaneously direct seeding both a large-grain restorer rice line as a male parent and a small-grain male sterile rice line as a female parent to allow the female plant to be pollinated by the male plant to produce $F_1$ progeny seed, wherein the large-grain restorer rice line is Wanghui 780 and has a 1000-grain weight of more than 30 g and a grain thickness of 2.2 mm or greater than 2.2 mm, and wherein the small-grain male sterile rice line has a 1000-grain weight of 8-22 g and a grain thickness of less than 2.1 mm;
   harvesting seeds produced by the male parent and the female parent to obtain mixed seeds; and
   according to a difference in a grain thickness, separating the seed produced by the male plant from the $F_1$ progeny seed produced by the female plant by screening and separating the mixed seeds with a screen, and wherein in a breeding process resulting in one or both of the parent lines used to make the $F_1$ progeny seed and each following breeding process between each generation, each generation from a first crossed hybrid generation is selected under a short-day low-temperature stress condition and a long-day low-temperature stress condition provided alternately from generation to generation.

2. The method for producing the hybrid rice seed according to claim 1, wherein;
   the Wanghui 780 is obtained through breeding, wherein the breeding comprises the following steps:
   crossing R9311 with Shuhui 498 to obtain a first breeding hybrid seed, breeding the first breeding hybrid seed and a second breeding hybrid seed, and mixed harvesting, and screening a seed with a 1000-grain weight of greater than 30 g, a grain thickness of greater than 2.2 mm, and a good rice quality from generations ranging from a third breeding generation to a fifth breeding generation for planting to obtain a next generation, wherein a seed of equal to or more than a sixth breeding generation is the large-grain restorer rice line.

3. The method for producing the hybrid rice seed according to claim 1, wherein, a manner of seeding the male parent and the female parent comprises a manner of seeding a sprouting rice as the male parent and a dry rice as the female parent, a manner of seeding a dry rice as the male parent and a sprouting rice as the female parent, a manner of seeding a first sprouting rice as the male parent and a second sprouting rice as the female parent, or a manner of seeding a first dry rice as the male parent and a second dry rice as the female parent.

4. The method for producing the hybrid rice seed according to claim 1, wherein, a manner of the direct-seeding is one selected from the group consisting of a manner of mixed direct-seeding the male parent and the female parent, a manner of drill direct-seeding the male parent and the female parent, and a manner of seedling-throwing the male parent and direct-seeding the female parent.

5. The method for producing the hybrid rice seed according to claim 1, wherein, a pore size of the screen has a width of 2.1 mm and a length of 20 mm.

6. The method producing the hybrid rice seed according to claim 1, wherein the short-day low-temperature stress condition includes a light period of less than 12 hours, and an average daily temperature of less than 23° C., and the long-day low-temperature stress condition includes a light period of greater than 12 hours, and an average daily temperature of less than 23° C.

7. The method producing the hybrid rice seed according to claim 1, wherein, the small-grain male sterile rice line is the seed of an $F_5$-$F_9$ generation plant.

* * * * *